United States Patent [19]
Bartley et al.

[11] Patent Number: 6,057,124
[45] Date of Patent: May 2, 2000

[54] NUCLEIC ACIDS ENCODING LIGANDS FOR HEK4 RECEPTORS

[75] Inventors: Timothy D. Bartley, Thousand Oaks; Gary M. Fox, Newbury Park, both of Calif.

[73] Assignee: Amgen Inc., Thousand Oaks, Calif.

[21] Appl. No.: 08/379,802

[22] Filed: Jan. 27, 1995

[51] Int. Cl.[7] .............................. C12N 15/12; C07K 14/47; C07K 5/10; C07K 15/63

[52] U.S. Cl. .................. 435/69.1; 435/71.2; 435/252.33; 435/320.1; 435/471; 536/23.5; 536/24.3; 935/11; 935/22; 935/70; 935/73

[58] Field of Search .................................. 435/69.1, 70.1, 435/70.3, 71.1, 71.2, 240.1, 240.2, 320.1, 252.3, 23.1, 252.33, 471; 935/22, 27, 29, 31, 52, 55, 56, 57, 66, 70, 72, 73; 536/23.5, 24.3

[56] References Cited

PUBLICATIONS

Kozlosky et al. Oncogene (Jan. 19, 1995) vol. 10. No. 2 pp. 299–306.

Fletcher et al. Oncogene (Nov. 1994) vol. 9. No. 11 pp. 3241–3247.

*Primary Examiner*—John Ulm
*Assistant Examiner*—Prema Mertz
*Attorney, Agent, or Firm*—Robert B. Winter; Steve M. Odre; Ron K. Levy

[57] ABSTRACT

Polypeptides which bind to one or more EPH-like receptors, particularly the HEK4 receptor, are described. The polypeptides are designated HEK4 binding proteins. Nucleic acids encoding HEK4 binding proteins, and expression vectors, host cells and processes for the production of the polypeptides are also described. The polypeptides are useful for modulating the growth and/or differentiation of a variety of tissues, including those from liver, kidney, lung, skin, digestive tract and nervous system and may be used to regenerate damaged or depleted tissue and to treat cancer or nervous system disorders.

8 Claims, 11 Drawing Sheets

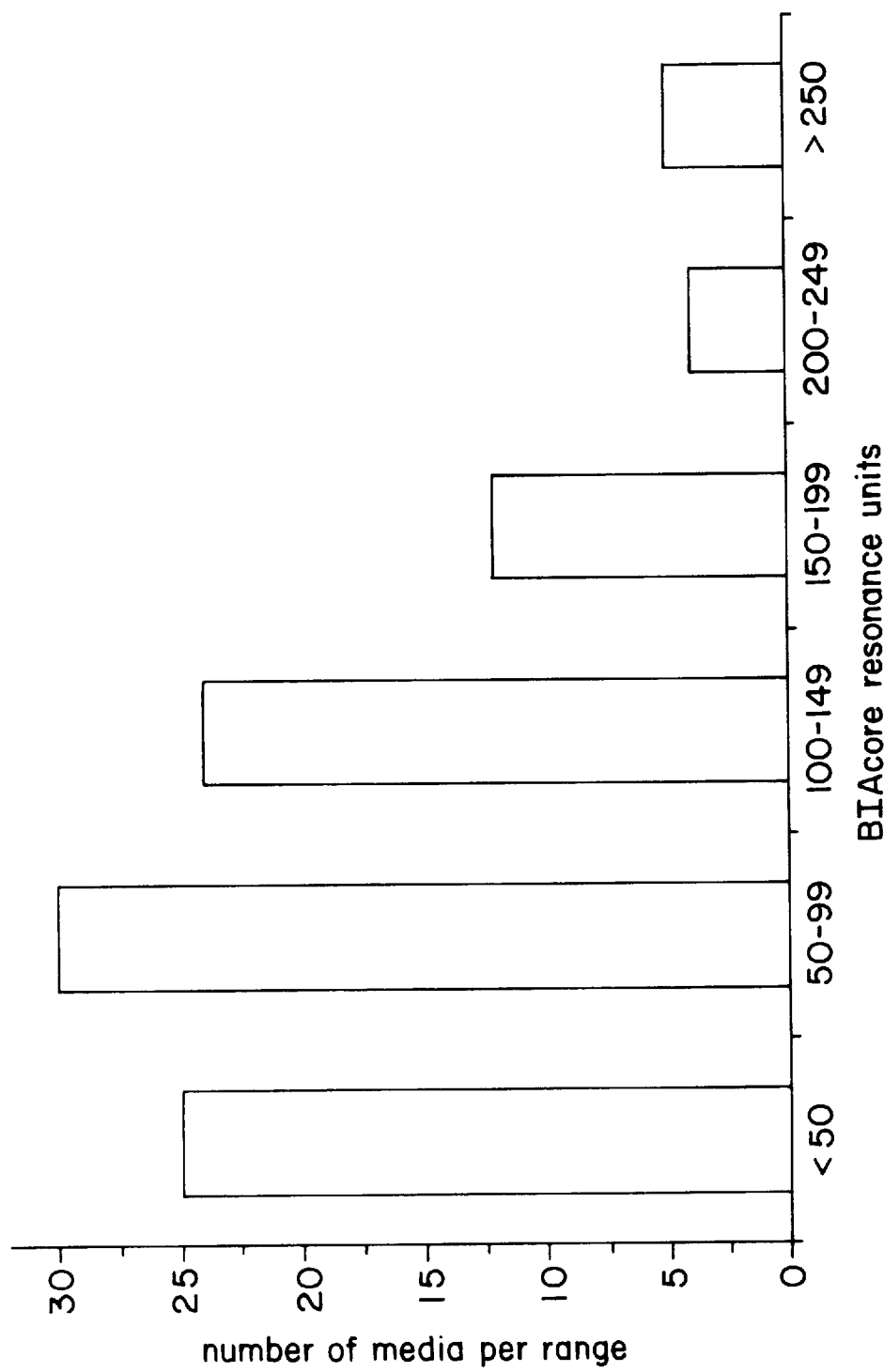

FIG. 3A

```
                10                              30                              50
GAATTCCCCCAGCTTGGTGGGCGCCTCTTTCCTTTCTCGCCCCCTTTCATTTTTATTTAT 70                              90                              110
TCATATTTATTTGGCGCCCGCTCTCTCTGTCCCTTTGCCTGCCTCCCTCCCTCCGGAT 130                             150                             170
CCCCGCTCTCTCCCCGGAGTGGCGCGTCGGGGGCTCCGCCGCTGGCCAGGCGTGATGTTG
                                                               M  L
                                                              -19
                190                             210                             230
CACGTGGAGATGTTGACGCTGGTGTTTCTGGTGCTCTGGATGTGTGTGTTCAGCCAGGAC
 H  V  E  M  L  T  L  V  F  L  V  L  W  M  C  V  F  S  Q  D
               -10                                         -1  1

250                             270                             290
CCGGGCTCCAAGGCCGTCGCCGACCGCTACGCTGTCTACTGGAACAGCAGCAACCCCAGA
 P  G  S  K  A  V  A  D  R  Y  A  V  Y  W  N  S  S  N  P  R
                     10                                         20

310                             330                             350
TTCCAGAGGGGTGACTACCATATTGATGTCTGTATCAATGACTACCTGGATGTTTTCTGC
 F  Q  R  G  D  Y  H  I  D  V  C  I  N  D  Y  L  D  V  F  C
                     30                                         40

370                             390                             410
CCTCACTATGAGGACTCCGTCCCAGAAGATAAGACTGAGCGCTATGTCCTCTACATGGTG
 P  H  Y  E  D  S  V  P  E  D  K  T  E  R  Y  V  L  Y  M  V
                     50                                         60

430                             450                             470
AACTTTGATGGCTACAGTGCCTGCGACCACACTTCCAAAGGGTTCAAGAGATGGGAATGT
 N  F  D  G  Y  S  A  C  D  H  T  S  K  G  F  K  R  W  E  C
                     70                                         80

490                             510                             530
AACCGGCCTCACTCTCCAAATGGACCGCTGAAGTTCTCTGAAAAATTCCAGCTCTTCACT
 N  R  P  H  S  P  N  G  P  L  K  F  S  E  K  F  Q  L  F  T
                     90                                        100

550                             570                             590
CCCTTTTCTCTAGGATTTGAATTCAGGCCAGGCCGAGAATATTTCTACATCTCCTCTGCA
 P  F  S  L  G  F  E  F  R  P  G  R  E  Y  F  Y  I  S  S  A
                     110                                       120

610                             630                             650
ATCCCAGATAATGGAAGAAGGTCCTGTCTAAAGCTCAAAGTCTTTGTGAGACCAACAAAT
 I  P  D  N  G  R  R  S  C  L  K  L  K  V  F  V  R  P  T  N
                     130                                       140
```

FIG. 3B

```
       670                    690                    710
AGCTGTATGAAAACTATAGGTGTTCATGATCGTGTTTTCGATGTTAACGACAAAGTAGAA
 S   C   M   K   T   I   G   V   H   D   R   V   F   D   V   N   D   K   V   E
                       150                                     160

730                    750                    770
AATTCATTAGAACCAGCAGATGACACCGTACATGAGTCAGCCGAGCCATCCCGCGGCGAG
 N   S   L   E   P   A   D   D   T   V   H   E   S   A   E   P   S   R   G   E
                       170                                     180

790                    810                    830
AACGCGGCACAAACACCAAGGATACCCAGCCGCCTTTTGGCAATCCTACTGTTCCTCCTG
 N   A   A   Q   T   P   R   I   P   S   R   L   L   A   I   L   L   F   L   L
                       190                                     200

850                    870                    890
GCGATGCTTTTGACATTATAGCACAGTCTCCTCCCATCACTTGTCACAGAAAACATCAGG
 A   M   L   L   T   L
                       209

910                    930                    950
GTCTTGGAACACCAGAGATCCACCTAACTGCTCATCCTAAGAAGGGACTTGTTATTGGGT 970                    990                    1010
TTTGGCAGATGTCAGATTTTTGTTTTCTTTCTTTCAGCCTGAATTCTAAGCAACAACTTC 1030                   1050                   1070
AGGTTGGGGGCCTAAACTTGTTCCTGCCTCCCTCACCCCACCCCGCCCCACCCCCAGCCC 1090                   1110                   1130
TGGCCCTTGGCTTCTCTCACCCCTCCCAAATTAAATGGACTCCAGATGAAAATGCCAAAT 1150                   1170                   1190
TGTCATAGTGACACCAGTGGTTCGTCAGCTCCTGTGCATTCTCCTCTAAGAACTCACCTC 1210                   1230                   1250
CGTTAGCGCACTGTGTCAGCGGGCTATGGACAAGGAAGAATAGTGGCAGATGCAGCCAGC 1270                   1290                   1310
GCTGGCTAGGGCTGGGAGGGTTTTGCTCTCCTATGCAATATTTATGCCTTCTCATTCAGA 1330                   1350                   1370
ACTGTAAGATGATCGCGCAGGGCATCATGTCACCATGTCAGGTCCGGAGGGGAGGGCCTA 1390                   1410                   1430
TCCCCCTATCCCAGGCATCCCAGACGAGGACTGGCTGAGGCTAGGCGCTCTCATGATCCA 1450                   1470                   1490
CCTGCCCCGGGAGGGCAGCGGGGAAGACAGAGAAAAGCAAAACGCATTCCTCCTCAGCTC 1510                   1530                   1550
CACCCACCTGGAGACGAATGTAGCCAGAGAGGAGGAAGGAGGGAAACTGAAGACACCGTG 1570                   1590                   1610
```

FIG.3C

GCCCCTCGGCCTTCTCTCTGCTAGAGTTGCCGCTCAGAGGCTTCAGCCTGACTTCCAGCG 1630                       1650                     1670
GTCCCAAGAACACCTACTAATTCTTCTCCACTCCTTCATGGCTGGGACAGTTACTGGTTC 1690                       1710
ATATGCAAGTAAAGATGACAATTTACTCAACAAAAAAAAAAGGAATTC

FIG.6A
FIG.6B
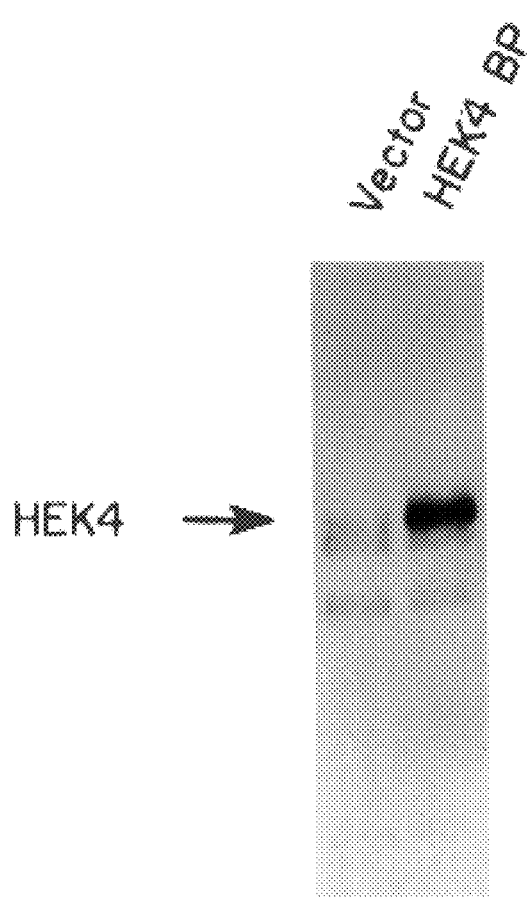
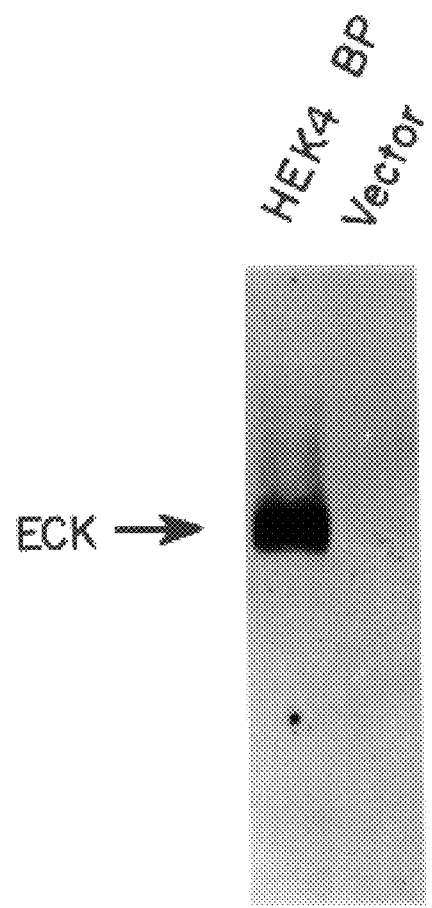

```
                          SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH: 1728 base pairs
         (B) TYPE: nucleic acid
         (C) STRANDEDNESS: single
         (D) TOPOLOGY: linear (ii) MOLECULE TYPE: cDNA (ix) FEATURE:
         (A) NAME/KEY: CDS
         (B) LOCATION: 175..858

(ix) FEATURE:
         (A) NAME/KEY: mat_peptide
         (B) LOCATION: 232..858

(ix) FEATURE:
         (A) NAME/KEY: sig_peptide
         (B) LOCATION: 175..231

(xi) SEQUENCE DESCRIPTION: SEQ ID NO:1:

GAATTCCCCC AGCTTGGTGG GCGCCTCTTT CCTTTCTCGC CCCCTTTCAT TTTTATTTAT      60

TCATATTTAT TTGGCGCCCG CTCTCTCTCT GTCCCTTTGC CTGCCTCCCT CCCTCCGGAT     120

CCCCGCTCTC TCCCCGGAGT GGCGCGTCGG GGGCTCCGCC GCTGGCCAGG CGTG ATG      177
                                                            Met
                                                            -19

TTG CAC GTG GAG ATG TTG ACG CTG GTG TTT CTG GTG CTC TGG ATG TGT      225
Leu His Val Glu Met Leu Thr Leu Val Phe Leu Val Leu Trp Met Cys
       -15                 -10                  -5
```

```
GTG TTC AGC CAG GAC CCG GGC TCC AAG GCC GTC GCC GAC CGC TAC GCT      273
Val Phe Ser Gln Asp Pro Gly Ser Lys Ala Val Ala Asp Arg Tyr Ala
              1               5                  10

GTC TAC TGG AAC AGC AGC AAC CCC AGA TTC CAG AGG GGT GAC TAC CAT      321
Val Tyr Trp Asn Ser Ser Asn Pro Arg Phe Gln Arg Gly Asp Tyr His
 15              20                  25                  30

ATT GAT GTC TGT ATC AAT GAC TAC CTG GAT GTT TTC TGC CCT CAC TAT      369
Ile Asp Val Cys Ile Asn Asp Tyr Leu Asp Val Phe Cys Pro His Tyr
                 35                  40                  45

GAG GAC TCC GTC CCA GAA GAT AAG ACT GAG CGC TAT GTC CTC TAC ATG      417
Glu Asp Ser Val Pro Glu Asp Lys Thr Glu Arg Tyr Val Leu Tyr Met
             50                  55                  60

GTG AAC TTT GAT GGC TAC AGT GCC TGC GAC CAC ACT TCC AAA GGG TTC      465
Val Asn Phe Asp Gly Tyr Ser Ala Cys Asp His Thr Ser Lys Gly Phe
         65                  70                  75

AAG AGA TGG GAA TGT AAC CGG CCT CAC TCT CCA AAT GGA CCG CTG AAG      513
Lys Arg Trp Glu Cys Asn Arg Pro His Ser Pro Asn Gly Pro Leu Lys
     80                  85                  90

TTC TCT GAA AAA TTC CAG CTC TTC ACT CCC TTT TCT CTA GGA TTT GAA      561
Phe Ser Glu Lys Phe Gln Leu Phe Thr Pro Phe Ser Leu Gly Phe Glu
 95                 100                 105                 110

TTC AGG CCA GGC CGA GAA TAT TTC TAC ATC TCC TCT GCA ATC CCA GAT      609
Phe Arg Pro Gly Arg Glu Tyr Phe Tyr Ile Ser Ser Ala Ile Pro Asp
                115                 120                 125

AAT GGA AGA AGG TCC TGT CTA AAG CTC AAA GTC TTT GTG AGA CCA ACA      657
Asn Gly Arg Arg Ser Cys Leu Lys Leu Lys Val Phe Val Arg Pro Thr
            130                 135                 140

AAT AGC TGT ATG AAA ACT ATA GGT GTT CAT GAT CGT GTT TTC GAT GTT      705
Asn Ser Cys Met Lys Thr Ile Gly Val His Asp Arg Val Phe Asp Val
        145                 150                 155

AAC GAC AAA GTA GAA AAT TCA TTA GAA CCA GCA GAT GAC ACC GTA CAT      753
Asn Asp Lys Val Glu Asn Ser Leu Glu Pro Ala Asp Asp Thr Val His
    160                 165                 170

GAG TCA GCC GAG CCA TCC CGC GGC GAG AAC GCG GCA CAA ACA CCA AGG      801
Glu Ser Ala Glu Pro Ser Arg Gly Glu Asn Ala Ala Gln Thr Pro Arg
175                 180                 185                 190

ATA CCC AGC CGC CTT TTG GCA ATC CTA CTG TTC CTC CTG GCG ATG CTT      849
Ile Pro Ser Arg Leu Leu Ala Ile Leu Leu Phe Leu Leu Ala Met Leu
                195                 200                 205

TTG ACA TTA TAGCACAGTC TCCTCCCATC ACTTGTCACA GAAAACATCA              898
Leu Thr Leu

GGGTCTTGGA ACACCAGAGA TCCACCTAAC TGCTCATCCT AAGAAGGGAC TTGTTATTGG    958

GTTTTGGCAG ATGTCAGATT TTTGTTTTCT TTCTTTCAGC CTGAATTCTA AGCAACAACT   1018

TCAGGTTGGG GGCCTAAACT TGTTCCTGCC TCCCTCACCC CACCCCGCCC CACCCCCAGC   1078

CCTGGCCCTT GGCTTCTCTC ACCCCTCCCA AATTAAATGG ACTCCAGATG AAAATGCCAA   1138

ATTGTCATAG TGACACCAGT GGTTCGTCAG CTCCTGTGCA TTCTCCTCTA AGAACTCACC   1198

TCCGTTAGCG CACTGTGTCA GCGGGCTATG GACAAGGAAG AATAGTGGCA GATGCAGCCA   1258

GCGCTGGCTA GGGCTGGGAG GGTTTTGCTC TCCTATGCAA TATTTATGCC TTCTCATTCA   1318

GAACTGTAAG ATGATCGCGC AGGGCATCAT GTCACCATGT CAGGTCCGGA GGGGAGGGCC   1378

TATCCCCCTA TCCCAGGCAT CCCAGACGAG GACTGGCTGA GGCTAGGCGC TCTCATGATC   1438

CACCTGCCCC GGGAGGGCAG CGGGGAAGAC AGAGAAAAGC AAAACGCATT CCTCCTCAGC   1498

TCCACCCACC TGGAGACGAA TGTAGCCAGA GAGGAGGAAG GAGGGAAACT GAAGACACCG   1558

TGGCCCCTCG GCCTTCTCTC TGCTAGAGTT GCCGCTCAGA GGCTTCAGCC TGACTTCCAG   1618
```

```
CGGTCCCAAG AACACCTACT AATTCTTCTC CACTCCTTCA TGGCTGGGAC AGTTACTGGT      1678

TCATATGCAA GTAAAGATGA CAATTTACTC AACAAAAAAA AAAGGAATTC                 1728
```

(2) INFORMATION FOR SEQ ID NO:2:

(i) SEQUENCE CHARACTERISTICS:
        (A) LENGTH: 228 amino acids
        (B) TYPE: amino acid
        (D) TOPOLOGY: linear (ii) MOLECULE TYPE: protein (xi) SEQUENCE DESCRIPTION: SEQ ID NO:2:

```
Met Leu His Val Glu Met Leu Thr Leu Val Phe Leu Val Leu Trp Met
-19          -15              -10                  -5

Cys Val Phe Ser Gln Asp Pro Gly Ser Lys Ala Val Ala Asp Arg Tyr
             1               5               10

Ala Val Tyr Trp Asn Ser Asn Pro Arg Phe Gln Arg Gly Asp Tyr
     15              20              25

His Ile Asp Val Cys Ile Asn Asp Tyr Leu Asp Val Phe Cys Pro His
 30              35              40                  45

Tyr Glu Asp Ser Val Pro Glu Asp Lys Thr Glu Arg Tyr Val Leu Tyr
             50              55                  60

Met Val Asn Phe Asp Gly Tyr Ser Ala Cys Asp His Thr Ser Lys Gly
             65              70              75

Phe Lys Arg Trp Glu Cys Asn Arg Pro His Ser Pro Asn Gly Pro Leu
         80              85              90

Lys Phe Ser Glu Lys Phe Gln Leu Phe Thr Pro Phe Ser Leu Gly Phe
     95              100             105

Glu Phe Arg Pro Gly Arg Glu Tyr Phe Tyr Ile Ser Ser Ala Ile Pro
110             115             120                 125

Asp Asn Gly Arg Arg Ser Cys Leu Lys Leu Lys Val Phe Val Arg Pro
             130             135             140

Thr Asn Ser Cys Met Lys Thr Ile Gly Val His Asp Arg Val Phe Asp
             145             150             155

Val Asn Asp Lys Val Glu Asn Ser Leu Glu Pro Ala Asp Asp Thr Val
             160             165             170

His Glu Ser Ala Glu Pro Ser Arg Gly Glu Asn Ala Ala Gln Thr Pro
             175             180             185

Arg Ile Pro Ser Arg Leu Leu Ala Ile Leu Leu Phe Leu Leu Ala Met
190             195             200             205

Leu Leu Thr Leu
```

(2) INFORMATION FOR SEQ ID NO:3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGATCTAGAG CACCAGCAAC ATGGATTGT                                         29
```

(2) INFORMATION FOR SEQ ID NO:4:

(i) SEQUENCE CHARACTERISTICS:

(A) LENGTH: 37 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TCGGTCTAGA TCATTATTGG CTACTTTCAC CAGAGAT                                37

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

Val Asn Phe Asp Gly Tyr Ser Ala Arg Asp
1               5                   10

(2) INFORMATION FOR SEQ ID NO:6:

(i) SEQUENCE CHARACTERISTICS:
        (A) LENGTH: 16 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

Val Phe Asp Val Asn Phe Lys Val Glu Xaa Ser Leu Glu Pro Ala Asp
1               5                   10                  15

(2) INFORMATION FOR SEQ ID NO:7:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:7:

Ala Val Ala Asp Arg Tyr Ala Val Tyr Trp Asn Ser Ser Asn Pro Arg
1               5                   10                  15

Phe Gln Arg Gly Asp Tyr His Ile Ile Val Xaa Ile Asn Xaa Tyr
            20                  25                  30

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

GAYMGNTAYG CNGTNTAYTG G                                                21

(2) INFORMATION FOR SEQ ID NO:9:

```
            (i) SEQUENCE CHARACTERISTICS:
                (A) LENGTH: 21 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:9:

RTANCCRTCR AARTTNACCA T                                                      21

(2) INFORMATION FOR SEQ ID NO:10:

(i) SEQUENCE CHARACTERISTICS:
                (A) LENGTH: 33 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:10:

GGAGGACATA TGAGCCAGGA CCCGGGCTCC AAG                                         33

(2) INFORMATION FOR SEQ ID NO:11:

(i) SEQUENCE CHARACTERISTICS:
                (A) LENGTH: 36 base pairs
                (B) TYPE: nucleic acid
                (C) STRANDEDNESS: single
                (D) TOPOLOGY: linear (ii) MOLECULE TYPE: cDNA (xi) SEQUENCE DESCRIPTION: SEQ ID NO:11:

GAAGAAGGAT CCCTATGGCT CGGCTGACTC ATGTAC                                      36
```

NUCLEIC ACIDS ENCODING LIGANDS FOR HEK4 RECEPTORS

The invention relates to polypeptides which bind to one or more EPH-like receptors. More particularly, the invention relates to polypeptides which bind to the HEK4 receptor, to nucleic acids encoding same and to expression vectors and host cells for the production of the polypeptides.

BACKGROUND OF THE INVENTION

The response of cells to their environment is often mediated by soluble protein growth and differentiation factors. These factors exert their effects by binding to and activating transmembrane receptors. This interaction is the initial event in a cascade which culminates in a biological response by the cell. An important class of transmembrane receptors is the receptor protein tyrosine kinases (receptor PTKs, reviewed in van der Geer et al. Ann. Rev. Cell. Biol. 10, 251–337 (1994). PTKs consist of an extracellular domain which interacts specifically with the receptor's cognate ligand, a membrane spanning domain, and an intracellular domain which harbors the tyrosine kinase activity. Receptor PTKs are activated by ligand-mediated dimerization followed by autophosphorylation of tyrosine residues in the cytoplasmic domain. The receptor PTK can then in turn phosphorylate substrate molecules in the signal transduction pathway, leading to a cellular response.

The family of receptor PTKs can be divided into a number of sub-families based on the general structure of the extracellular domain and on amino acid sequence relationships within the catalytic domain. Currently, the largest known sub-family of receptor protein tyrosine kinases is the EPH-like receptors, consisting of at least 13 members. Members of this sub-family include the following: EPH (Hirai et al., Science 238, 1717–1725 (1987)), ECK (Lindberg et al., Mol. Cell. Biol. 10, 6316–6324 (1990)), Cek4, Cek5, Cek6, Cek7, Cek8, Cek9, Cek10 (Pasquale, Cell Regulation 2, 523–534 (1991); Sajjadi et al., The New Biologist 3, 769–778 (1991); Sajjadi and Pasquale Oncogene 8, 1807–1813 (1993)), Eek, Erk (Chan and Watt, Oncogene 6, 1057–1061 (1991)), Ehk1, Ehk2 (Maisonpierre et al., oncogene 8, 3277–3288 (1993)), HEK (PCT Application No. WO93/00425; Wicks et al., PNAS 89, 1611–1615 (1992)), HEK2 (Bohme et al., Oncogene 8, 2857–2862 (1993)), HEK5, HEK7, HEK8, HEK11 (U.S. Ser. No. 08/229,509) and HTK (Bennett et al. J. Biol. Chem. 269, 14211–14218 (1994)).

Until recently, no ligands for any member of the EPH sub-family had been identified. A ligand for the Eck receptor was described in PCT Application No. WO 94/11020 and Bartley et al. (Nature 368, 558–560 (1994)) and identified earlier as B61, a polypeptide encoded by a cDNA of unknown function (Holzman et al., Mol. Cell Biol. 10, 5830–5838 (1990)). Ligands for Elk and Ehk1 receptors have also been reported (PCT Application No. WO094/11384; Davis et al., Science 266, 816–819 (1994)). Most recently, a polypeptide (ELF-1) identified from a mouse embryo midbrain and hindbrain cDNA library has been reported to be a ligand for Mek4 and Sek (Cheng and Flanagan, Cell 79, 157–168 (1994).

Most attempts to purify soluble factors from complex biological fluids have depended on cell-based bioassays of the response to stimulation by the factor. These include increased cell growth or survival, increased DNA synthesis, a chemotactic response, or some other downstream consequence of receptor activation. Receptor autophosphorylation has also been used as an assay to detect stimulation of the cell. We have recently described a method for the isolation of ligands based on direct detection of receptor/ligand binding and the use of receptor affinity chromatography for purification (Bartley et al., supra). Here we report the application of this method to purify, sequence, and molecularly clone one of a family of ligands corresponding to the EPH sub-family of receptor tyrosine kinases.

Although the EPH sub-family is the largest known sub-family of receptor PTKs, few ligands have been identified which bind to and activate an EPH sub-family receptor. It is therefore an objective to identify additional ligands for EPH sub-family receptor PTKs. These ligands will be useful for modulating responses of EPH sub-family receptor bearing cells.

SUMMARY OF THE INVENTION

The present invention relates to polypeptides capable of binding to one or more EPH-like receptor PTKs. More particularly, the invention provides polypeptides which bind to the HEK4 receptor, but may also bind to other members of the sub-family of EPH-like receptor PTKs. These polypeptides are referred to as HEK4 binding proteins (HEK4 BPs). In one embodiment, the polypeptide binds to and activates HEK4 and ECK receptors. Also encompassed by the invention are nucleic acids encoding HEK4 BPs and nucleic acids which hybridize to HEK4 BP nucleic acids and encode polypeptides having at least one of the biological properties of a HEK4 BP. Biologically active HEK4 BP fragments and analogs and nucleic acids encoding same as well as fusion proteins comprising HEK4 BP are also encompassed by the invention.

Expression vectors and host cells for the production of biologically active HEK4 BP and processes for the production of HEK4 BP using the expression vectors and host cells are also within the scope of the invention. Antibodies specifically binding HEK4 BP are also provided for.

Polypeptides of the invention are useful for modulating (i.e., increasing or decreasing) the growth and/or differentiation of EPH sub-family receptor-bearing cells, particularly cells expressing HEK4 or ECK receptors. Based on levels of expression of HEK4, ECK, and HEK4 BP in a variety of tissues, it is expected that HEK4 BP will be useful for modulating the growth and/or differentiation, for example, liver, kidney, lung, skin or neural tissues. Administration of HEK4 BP to mammals is useful in the treatment of nervous system disorders and in the regeneration of damaged or depleted tissues. HEK4 BP antagonists are also useful for the treatment of cancers.

DESCRIPTION OF THE FIGURES

FIG. 1. BIAcore screening of conditioned media on HEK4-X surface. Concentrated samples of cell-conditioned media were screened on a HEK4-X surface as described in Example 2. The number of conditioned media samples giving a signal within each range of resonance units (RU) are shown in the histogram. Samples which bound more than 200 RU are summarized in Table 1.

FIGS. 3A–C. Sequence of HEK-4 binding protein cDNA. The nucleic acid sequence of the human HEK-4 binding protein cDNA clone containing the entire coding sequence is shown along with the predicted amino acid sequence. The cDNA clone predicts a protein of between 213 and 228 amino acids, depending on which of three potential start codons is utilized. The sequence is numbered so that the predicted mature N-terminal amino acid is residue 1, with the putative signal peptide (underlined) extending from residues −19 to −1.

FIGS. 6A and 6B. Stimulation of tyrosine phosphorylation of EPH-like receptors by membrane-bound HEK4 BP. CHO cells that express recombinant HEK4 receptor and endogenous ECK were treated with cells that were transfected with an expression vector that contained the HEK4 BP cDNA or vector without cDNA. After lysis, HEK4 receptor (A) or ECK receptor (B) were immunoprecipitated. The immunoprecipitates were fractionated by PAGE, electroblotted, and probed with antiphosphotyrosine antibodies.

DETAILED DESCRIPTION OF THE INVENTION

Figure 2A:
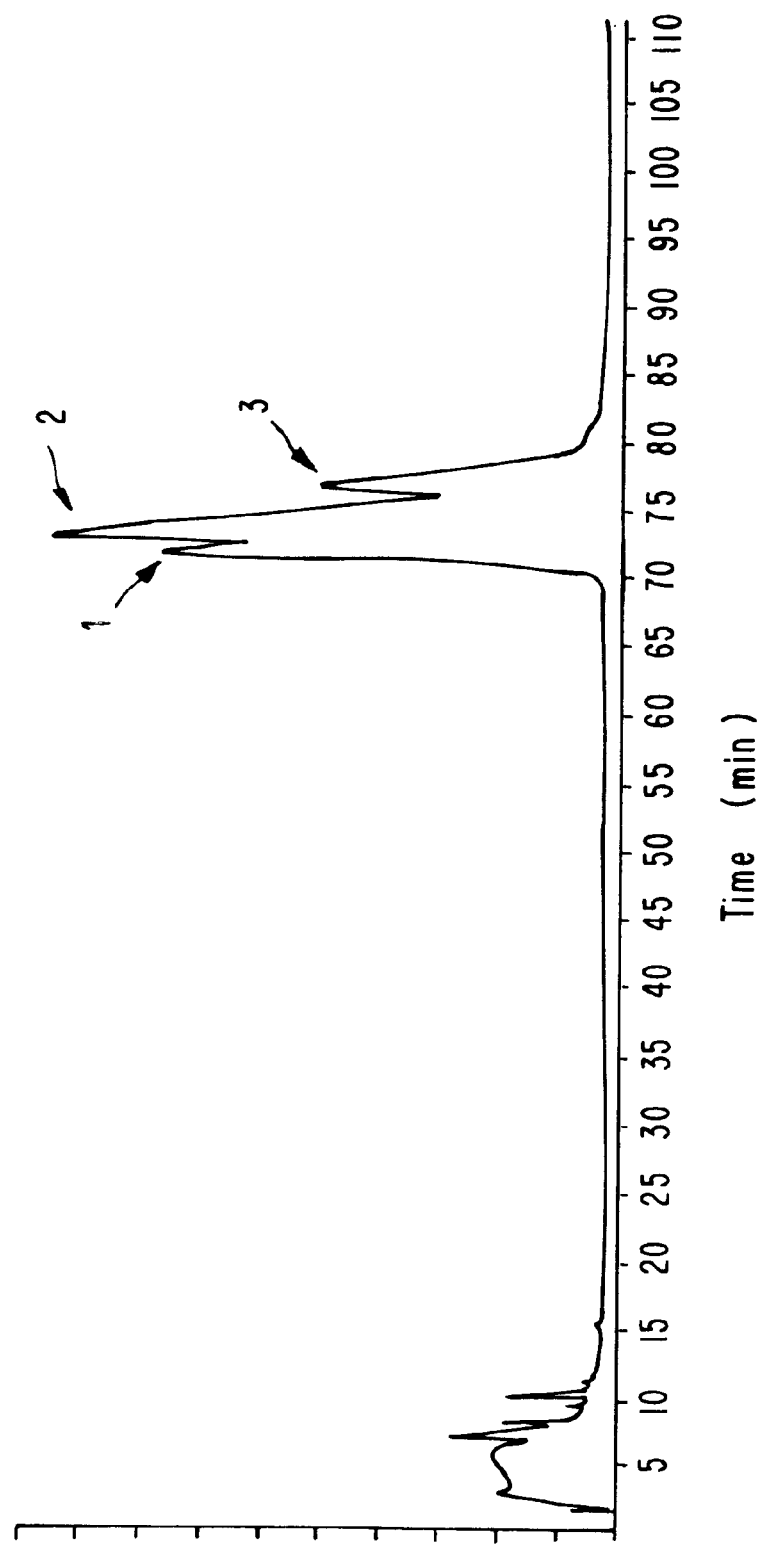
FIGS. 2A and 2B. Purification of HEK4 Binding Protein from A498 conditioned media. C4 Reverse Phase HPLC column profile of HEK4 BP (A); SDS-PAGE analysis of pools of indicated peaks observed on the C4 column (B).

The present invention relates to polypeptides capable of binding to one or more EPH-like receptor PTKs and, more particularly, are capable of binding to a human homolog of an EPH-like receptor PTK. To date, eight human homologs of EPH-like receptors have been identified: EPH, ECK, HTK, HEK2, HEK4, HEK5, HEK7, HEK8 and HEK11. Characteristics of several HEK receptors are disclosed in co-pending and commonly owned U.S. Ser. No. 08/229,509 herein incorporated by reference. The polypeptides of the present invention preferentially bind HEK4 receptor and are referred to herein as HEK4 binding proteins (HEK4 BP). The HEK4 receptor is a glycosylated 135 kDa protein tyrosine kinase previously identified as HEK receptor by Wilks et al. supra, and is the human homolog of the Cek 4 and Mek 4 receptors identified in chicken and mouse, respectively. Polypeptides capable of binding HEK4 receptor may also activate the receptor by inducing receptor autophosphorylation, an event which initiates transmission of a signal from the cell surface to the nucleus. Activation of HEK4 receptors leads to modulation of growth and/or differentiation of HEK4 receptor-bearing cells. HEK4 BP also binds to and activates other EPH-like receptors as described below.

A HEK4 binding protein has been identified and isolated from A498 cell line conditioned medium by procedures generally described in U.S. Ser. No. 08/145,616, relevant portions of which are herein incorporated by reference, and described in more detail in Example 2. Briefly, a gene encoding the extracellular domain of the HEK4 was constructed and expressed as described in Example 1. The purified HEK4 extracellular domain was immobilized on a BIAcore sensor chip and concentrated conditioned media from 102 different cell lines were screened for binding to HEK4 receptor extracellular domains by surface plasmon resonance. This procedure identified conditioned medium from several cell lines shown in Table 1 having one or more factors which interacted with HEK4. The A498 cell line was chosen as a source for HEK4 ligand and a protein binding to HEK4 was purified as described in Example 2. Purified and isolated HEK4 binding protein from A498 cell-conditioned medium has three major forms of molecular weights 21, 25 and 27 kD on nonreducing SDS-polyacrylamide gels. These forms represent glycosylation and C-terminal processing variants. HEK4 BP has the amino acid sequences as shown in Table 2 for the peptides generated by cyanogen bromide or trypsin cleavage.

cDNA clones of HEK4 binding protein were obtained from a human placenta cDNA library as described in Example 3. The sequence of human HEK4 binding protein cDNA is shown in FIGS. 3A–C. Based upon cDNA sequencing and carboxy-terminal peptide mapping of the A498 cell-derived protein, a major secreted form of HEK4 binding protein had an amino terminal serine residue as shown in FIGS. 3A–C and a carboxy terminal proline residue at position 179. An alternate secreted form having a carboxy terminal alanine residue at position 177 was also detected. Alternative forms of HEK4 BP, including membrane-bound forms, may also be synthesized.

Figure 7A:
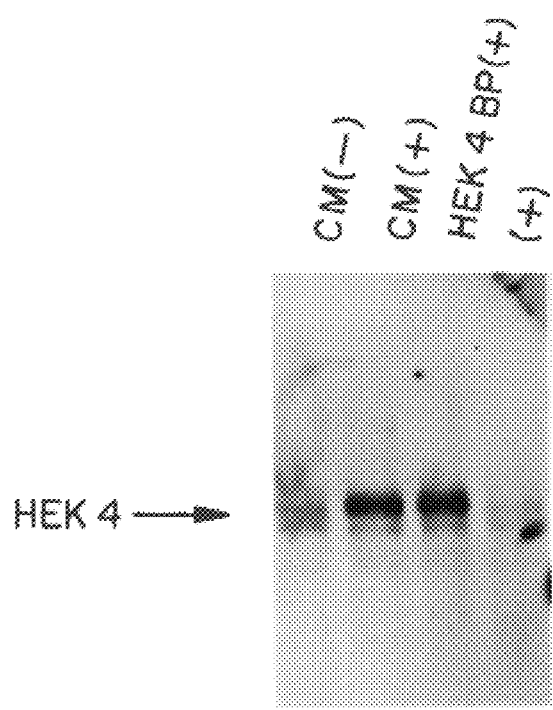
FIG. 7. Stimulation of tyrosine phosphorylation by soluble HEK4 BP. Cells were treated with conditioned media (CM) or recombinant HEK4 BP, with (+) or without (−) antibody clustering, and assayed for HEK4 receptor activation. A) Twelve-fold concentrated media was compared to 2 μg/ml HEK4 BP. (B) A dose response comparing clustered and unclustered HEK4 BP.
Figure 7B:
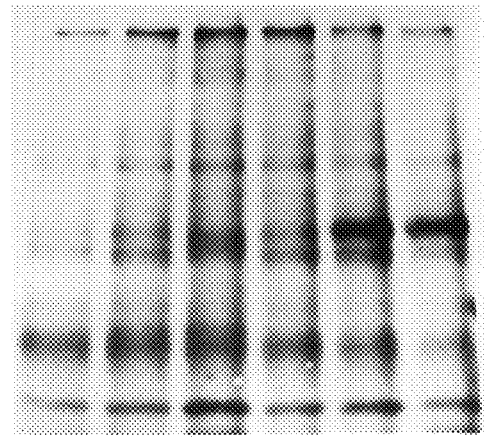

Recombinant HEK4 binding protein was expressed in CHO cells transfected with cDNA encoding HEK4 BP as shown in FIGS. 3A–C. Soluble HEK4 BP was purified as described in Example 4 and shown to bind HEK4 receptor by BIAcore analysis. Purified soluble HEK4 BP activated HEK4 receptor and this activation was enhanced by antibody clustering of the ligand (FIGS. 7A, 7B). Activation of HEK4 receptor was also observed upon contact of CHO cells expressing HEK4 BP with CHO cells expressing HEK4 receptor (FIGS. 6A, 6B). Therefore, recombinant HEK4 binding protein binds and activates EPH-like receptor PTKs.

The invention provides for a purified and isolated polypeptide, termed HEK4 binding protein, capable of binding at least one EPH-like receptor. In one embodiment, the polypeptide is capable of binding the HEK4 receptor. HEK4 binding protein is mammalian and is preferably human. Purified HEK4 binding protein is substantially free of other human proteins and has a molecular weight of about 21 to 27 kD on nonreducing SDS-PAGE. HEK4 BP has at least about 70% homology to the amino acid sequence as shown in FIGS. 3A–C (SEQ ID NO: 1) and is capable of binding at least one EPH-like receptor. Preferably, HEK4 BP has the amino acid sequence as shown in FIGS. 3A–C (SEQ ID NO: 1). Binding of an EPH-like receptor by HEK4 BP may or may not result in receptor activation. EPH-like receptor binding and activation may be effected by either soluble or membrane-bound form of HEK4 BP, or by both forms. It is further understood that receptor binding and activation by HEK4 BP is not restricted to HEK4 receptor, but that HEK4 BP may also bind to and activate other EPH-like receptor family members. As described in Example 7, HEK4 binding protein has been shown to activate both HEK4 and ECK receptors.

HEK4 binding proteins of the invention are preferably characterized by being the product of procaryotic or eucaryotic expression of an exogenous DNA sequence, i.e., HEK4 binding protein is a recombinant protein. Exogenous DNA is DNA which encodes HEK4 binding protein and includes cDNA, genomic DNA and synthetic (manufactured) DNA. HEK4 binding protein may be expressed in bacterial, yeast, plant, insect or mammalian cells in culture or in transgenic animals using DNA expression vectors appropriate for the given host cell. Expression of recombinant HEK4 binding protein in CHO cells is described in Example 3A, 3B, 3C of the specification.

Also provided is HEK4 BP in dimeric or higher order oligomeric states wherein multimeric HEK4 BP is capable of binding and/or activating EPH-like receptors. Soluble HEK4 BP multimers are selected from the group consisting of HEK4 BP/immunoglobulin chimeras, HEK4 BP clustered by treatment with anti-HEK4 BP antibodies, and covalently and noncovalently attached HEK4 BP monomers. Clustered HEK4 BP is described in Example 7B and HEK4 BP chimeras are constructed using standard recombinant DNA techniques. Covalently and noncovalently attached HEK4 BP monomers are produced using protein crosslinking reagents and procedures readily available to one skilled in the art.

The polypeptides of the present invention include biologically active fragments and analogs of HEK4 BP. HEK4 BP fragments encompass amino acid sequences having truncations of one or more amino acids from the sequence shown in FIGS. 3A, 3B, 3C or in SEQ ID NO: 1, wherein the truncation may originate from the amino terminus, carboxy terminus, or from the interior of the protein. Analogs of the invention involve an insertion or a substitution of one or more amino acids within the sequence as shown in FIGS. 3A–C or SEQ ID NO: 1. Fragments and analogs will have at least one biological property of HEK4 binding protein, typically the ability to bind at least one EPH-like receptor.

Also encompassed by the invention are chimeric polypeptides comprising HEK4 BP amino acid sequences fused to heterologous amino acid sequences. Said heterologous sequences encompass those which, when formed into a chimera with HEK4 BP, retain one or more biological or immunological properties of HEK4 BP. In one embodiment, a HEK4 BP/immunoglobulin chimeric protein is encompassed wherein chimeric molecules may aggregate to multimeric forms of HEK4 BP for receptor binding and activation. One example is a chimera of HEK4 BP and the Fc region of IgG.

Also provided by the invention is an isolated nucleic acid encoding HEK4 binding protein. The nucleic acid is selected from the group consisting of:
  a) the nucleic acid as shown in FIGS. 3A–C (SEQ ID NO: 1);
  b) nucleic acids which hybridize under conditions of 6×SSC and 65° C. with the coding regions as shown in FIGS. 3A, 3B, 3C (SEQ ID NO: 1);
  c) nucleic acids which are degenerate to the nucleic acids of (a) and (b). The nucleic acids may be cDNA, genomic DNA or synthetic (manufactured) DNA. It is understood that the hybridization conditions specified herein allow one skilled in the art to estimate the extent of mismatch between a given nucleic acid and a nucleic acid comprising the coding region as shown in FIGS. 3A–C (SEQ ID NO: 1) and that such conditions may be varied by changing salt, temperature and/or length of incubation or adding organic solvent at either the washing or hybridization steps and still allow one to obtain an equivalent level of mismatch during hybridization. Therefore, it is envisioned that the nucleic acids of the invention include those which hybridize with the coding regions in FIGS. 3A–C under conditions equivalent to those of 6×SSC and 65° C. Nucleic acid sequences encoding HEK 4 binding protein may have an amino terminal leader sequence and a carboxy terminal membrane anchor sequence or alternatively, may have one or both sequences removed. The encoded polypeptides will have at least one of the biological properties of HEK4 BP.

The nucleic acids of the invention will be operatively linked with nucleic acid sequences so as to express HEK4 binding protein. Sequences required for expression are known to those skilled in the art and include promoters and enhancer sequences for initiation of transcription, transcription termination sites, ribosome binding sites, and sequences directing polypeptide secretion. A general description of nucleic acid sequences which serve to direct expression of exogenous genes is found in *Methods in Enzymology* v. 185, D. V. Goeddel, ed. Academic Press, Inc. New York (1990). Sequences directing expression of HEK4 binding protein may be homologous or heterologous. A variety of expression vectors may be used to express HEK4 binding protein in procaryotic or eucaryotic cells in culture. One such vector is pDSRα described in PCT Application No. WO90/14363 which was used to express HEK4 BP in CHO cells (see Example 3). In addition, vectors for tissue-specific expression of HEK4 binding protein in transgenic animals and viral-based gene transfer vectors for expression of HEK4 binding protein in human cells in vivo are also available. The nucleic acid coding regions of HEK4 binding protein may be modified by substitution of preferred codons for optimal expression in an appropriate host cell using procedures available to the skilled worker.

Plasmid pDSRα containing the nucleic acid sequence encoding HEK4 BP as shown in FIGS. 3A, 3B, 3C has been deposited with the American Type Culture Collection, Rockville, Md. on Jan. 20, 1995, under ATCC Accession No. 97028.

A host cell transformed or transfected with nucleic acids encoding HEK4 binding protein are also encompassed by the invention. Any host cell which produces a polypeptide having at least one of the biological properties of a HEK4 BP may be used. Specific examples include bacterial, yeast, plant, insect or mammalian cells. In addition, HEK4 binding protein may be produced in transgenic animals. Transformed or transfected host cells and transgenic animals are obtained using materials and methods that are routinely available to one skilled in the art. Host cells may contain nucleic acid sequences having the full-length gene for HEK4 binding protein including a leader sequence and a C-terminal membrane anchor sequence (as shown in FIGS. 3A–C) or, alternatively, may contain nucleic acid sequences lacking one or both of the leader sequence and the C-terminal membrane anchor sequence. In addition, nucleic acid fragments, variants and analogs which encode a polypeptide capable of binding HEK4 receptor may also be resident in host expression systems. Polypeptides of the invention are produced by growing transformed or transfused host cells under suitable nutrient conditions to express HEK4 BP and isolating the results at polypeptides.

Antibodies specifically binding HEK4 binding proteins of the invention are also encompassed. The antibodies can be produced by immunization with full-length (unprocessed) HEK4 binding protein or its mature forms or a fragment thereof. Antibodies may be polyclonal or monoclonal and may be human or murine-derived. Antibodies of the invention may also be recombinant, such as chimeric antibodies having the murine constant regions on the light and heavy chains replaced by human constant region sequences; or complementary determining region (CDR)-grafted antibodies wherein only the CDR is of murine origin and the remainder of the antibody chain has been replaced by human sequences.

The invention also provides for a pharmaceutical composition comprising a therapeutically effective amount of HEK4 binding protein and a pharmaceutically acceptable adjunct. Examples of pharmaceutically acceptable adjuncts include diluents (Tris, acetate or phosphate buffers), carriers (human serum albumin), solubilizers (Tween, polysorbate), preservatives (thimerosol, benzyl alcohol) and anti-oxidants (ascorbic acid). A more extensive survey of components typically found in pharmaceutical compositions appears in *Remington's Pharmaceutical Sciences* 18th ed. A. R. Gennaro, ed. Mack, Easton, Pa. (1990). As used herein, the term "therapeutically effective amount" refers to that amount of HEK4 binding protein which provides a therapeutic effect for a given condition and administration regimen. Said therapeutically effective amount may vary from 0.01 μg/kg body weight to 10 mg/kg body weight and may be determined by one skilled in the art.

HEK4 binding protein may be administered by injection, either subcutaneous, intravenous or intramuscular, or by oral or nasal administration. The route of administration to be chosen will depend upon several variables, including the nature and severity of the condition being treated and the pharmacokinetic properties of the HEK4 binding protein preparation. HEK4 binding protein may be formulated for delivery in a particular fashion, e.g., it may be modified with water soluble polymers, such as polytheylene glycol to improve properties for nasal delivery or to improve serum half-life after injection; or it may be incorporated into particulate preparations of polymeric compounds (e.g., liposomes) for controlled delivery over an extended period of time.

The expression of HEK4 receptor and HEK4 BP in various tissues is reported in Examples 6A and 6B, respectively. HEK4 receptor mRNA was most abundant in human placenta and was also detected in heart, brain, lung, liver, muscle, kidney tissues. HEK4 BP mRNA was most abundant in human adult brain, kidney and placenta, and was detected at lower levels in heart, lung, liver, spleen, prostate, testis, ovary, small intestine, muscle, pancreas and colon. These patterns of expression suggest that activation of HEK4 receptor by HEK4 BP modulates the growth and/or differentiation of a variety of target cells, particularly those in the brain, heart, lung, liver, muscle and pancreas where expression of both receptor and ligand are detected. In addition, Wicks et al., supra has reported HEK4 receptor mRNA in pre-B and T cell lines, suggesting a role for HEK4 BP in hematopoiesis.

As described in Example 7, HEK4 BP also activates ECK receptor in a cell-cell autophosphorylation assay. Eck receptor mRNA is most abundant in adult rat lung, small intestine, kidney, ovary and skin with lower levels detected in brain, spleen and submaxillary gland (Lindberg and Hunter, supra).

Recently, it has been shown that Eck is expressed in the nervous system of the early mouse embryo (Becker et al. Mech. Dev. 47, 3–17 (1994); Ganju et al. Oncogene 9, 1613–1624 (1994)). These observations suggest that activation of ECK receptor by HEK4 BP may modulate the growth and/or differentiation of cells expressing ECK, such as those in the lung, intestine, kidney, skin and nervous system.

Therefore, HEK4 BP is useful in modulating (i.e., increasing or decreasing) the extent of growth and/or differentiation of target cells in various tissues. The target cells will have at least one receptor which is activated by HEK4 BP wherein the receptor is preferably a member of the EPH sub-family of receptor PTKs. Potential therapeutic uses for HEK4 BP are described below.

One aspect of the invention is the use of HEK4 BP to modulate cell growth and differentiation in the nervous system. HEK4 BP may be used to maintain or restore cellular function in the nervous system of a mammal which has been decreased or eliminated by disease or injury or is at risk of being decreased or eliminated by disease or injury. Target cells include neurons and glial cells. Conditions that may be treated by HEK4 BP include central nervous system disorders such as Alzheimer's disease, Parkinson's disease, multiple sclerosis, stroke and Huntington's disease and peripheral nervous system disorders such as amyotrophic lateral sclerosis (ALS) and peripheral neuropathies. Physical injuries to the spinal cord and to peripheral neurons may also be treated with HEK4 BP.

Another aspect of the invention is the modulation by HEK4 BP of growth and differentiation of digestive tract (including large and small intestine), liver, lung, pancreas, muscle and hematopoietic tissues. This activity of HEK4 BP may be particularly useful in regeneration of tissue in these and other sources which has been damaged or depleted by disease or injury.

It has been observed that the sub-family of EPH-like receptors and their corresponding ligands are highly expressed in some carcinoma cell lines (see for example, PCT Application No. WO94/11020 for expression of ECK receptor and ECK binding protein in human carcinoma cell lines). Thus another aspect of the invention is the treatment of cancers using HEK4 BP antagonists to block cell proliferation. Such cancers are likely to be associated with organs which express HEK4 receptors and/or Eck receptors. HEK4 BP antagonists may be any compound which blocks the biological activity of HEK4 BP and may include, but are not limited to, the following: antibodies which bind to either HEK4 BP or to an EPH sub-family receptor which is activated by HEK4 BP such that a receptor/ligand interaction is prevented; HEK4 BP which binds to, but does not activate and EPH-like receptor; and soluble EPH-like receptors which bind to HEK4 BP. It is envisioned that small molecule mimetics of the above described antagonists are also encompassed by the invention.

In addition to in vivo applications, HEK4 BP may also be used ex vivo to amplify cell populations prior to transplantation. It is envisioned that HEK4 BP may promote growth in culture of cells from the digestive tract, liver, lung, bone marrow, kidney, or central and peripheral nervous systems (and glial cells) neurons such that the amplified population can be introduced back into a patient in need of such therapy. Such so-called "cell therapy" is useful in replenishing cells after damage or depletion and may be appropriate under conditions where systemic administration of HEK4 BP is not preferred.

HEK4 BP may be used alone or in combination with other therapeutic agents for the treatment of cancer, neurological disorders, disorders of the digestive tract, liver, or lung, and for the ex vivo expansion of cell populations. HEK4 BP may be used in conjunction with other chemotherapeutic drugs or with radiation therapy for the treatment of cancer, or with other neurotrophic factors such as brain derived neutrophic factor (BDNF), ciliary neurotrophic factor (CNTF), neurotrophin-3 (NT-3), nerve growth factor (NGF), or glial derived neurotrophic factor (GDNF) for neurological disorders; or with tissue growth factors such as platelet derived growth factor (PDGF), fibroblast growth factor (FGF), epidermal growth factor (EGF), hepatocyte growth factor (HGF) or keratinocyte growth factor (KGF) for restoration of damaged or depleted tissues.

Isolated nucleic acids of the present invention are useful reagents for the detection and quantitation of DNA and/or RNA coding for HEK4 BP by standard hybridization procedures such as those described in Sambrook et al. *Molecular Cloning, A Laboratory Manual*, 2d ed. Cold Spring Harbor Laboratory Press, Cold Spring Harbor, N.Y. (1989). These reagents allow one to determine the potential of various cell types to express HEK4 BP and related polypeptides and are also useful for detecting abnormalities in genes encoding HEK4 BP or in sequences controlling the expression of HEK4 BP. Nucleic acids of the invention are also useful for controlling expression levels of HEK4 BP. So-called "anti-sense" nucleic acids hybridize to DNA and/ or RNA strands encoding HEK4 BP in a manner that blocks transcription or translation of HEK4 BP nucleic acid sequences. Introduction of HEK4 BP anti-sense nucleic acids into cells overexpressing HEK4 BP is appropriate when such overexpression leads to undesirable physiological effects, such as excessive cell proliferation.

Antibodies which specifically bind HEK4 BP are useful reagents for the detection and quantitation of HEK4 BP in biological samples using immunoassays (Western blots, RIAs, ELISAs) that are conventional to the art. The presence of HEK4 BP may be indicative of cell proliferation or the potential for cell proliferation, and elevated levels may signal abnormal cell growth typically associated with cancer. In addition, antibodies of the invention may also be useful therapeutic reagents that act as agonists or antagonists of HEK4 BP activity. Antibodies may bind to HEK4 BP in a manner that directly or indirectly blocks HEK4 BP binding an EPH receptor (either HEK4 or ECK). Alternatively, antibodies may bind to HEK4 BP in a manner which promote receptor binding and activation by, for example, "clustering" HEK4 BP into a dimeric or higher multimeric forms to allow more efficient binding and activation of receptor. Antibodies can be monoclonal, polyclonal, or recombinant.

The following examples are offered to more fully illustrate the invention, but are not construed as limiting the scope thereof.

EXAMPLE 1

Production of HEK4 Receptor Extracellular Doman (HEK4-X)

A cDNA clone coding for the HEK4 receptor protein tyrosine kinase was isolated from a human fetal brain cDNA library (Stratagene, La Jolla, Calif.) as described in co-pending and commonly owned U.S. Ser. No. 08/229,509. The sequence of this clone was identical to that in FIGS. 1 of Wicks et al., supra with the following exceptions. Wicks reported the sequence TTA at nucleotides 1618–1620 whereas the HEK4 receptor clone isolated as described here had the sequence TTC at these positions. However, Wicks et al.'s predicted protein sequence specifies a phenylalanine residue in this position, which is inconsistent with an "A" at nucleotide 1620 (TT<u>A</u> codes for leucine while TT<u>C</u> codes for phenylalanine). Also, nucleotides 1529 through 1531 of the Wicks et al. sequence are absent from the sequence obtained here. This change does not affect the translational reading frame, but does eliminate the predicted glutamine residue at position 478 of the Wicks sequence. The effect of these differences on the biological activity of the receptor or the ability to bind ligand is unknown.

The HEK4 receptor cDNA clone was used as a template in a polymerase chain reaction (PCR) designed to amplify a DNA fragment coding for the ligand binding domain of the HEK4 receptor. The primers used were:

433-26) 5' GGATCTAGAGCACCAGCAACATGGATTGT 3' (SEQ ID NO: 3)

409-10) 5' TCGGTCTAGATCATTATTGGC- TACTTTCACCAGAGAT 3' (SEQ ID NO: 4)

These primers produce a fragment 1656 nucleotides in length that codes for a protein of 540 amino acids. The predicted protein consists of the entire extracellular domain of the HEK4 receptor from the amino terminus up to but not including the transmembrane region. The 1656 nucleotide fragment was digested with the restriction endonuclease XbaI and ligated into the expression vector pDSRα which had been digested with the same enzyme. The resulting expression plasmid was introduced into CHO cells by calcium phosphate mediated transfection (Cellphect, Pharmacia, Piscataway, N.J.). Individual colonies were selected based upon the expression of the dihydrofolate reductase (DHFR) gene which resides on the expression plasmid. Expression of the HEK4 gene was monitored by RNA solution hybridization (Hunt et al. Exp. Hematol. 19, 779–784 (1991)) and/or by Western blotting with antibodies directed against amino acids 22–148 of the HEK4 extracellular domain.

HEK4 expression was enhanced by growth of the selected clones in 100 nM methotrexate. One of the pDSRα/HEK4-X clones was chosen for large scale production. Twenty-four roller bottles were seeded at a density of approximately $2\times10^7$ cells/bottle in 200 ml each of Dulbecco's Minimal Essential Media (DMEM) supplemented with non-essential amino acids (1× NEAA, Gibco), 100 nM methotrexate, 1× penicillin/streptomycin/glutamine (1× PSG, Gibco) and 10% fetal bovine serum. Cells reached confluence in 3–4 days at which time the media was changed to DMEM/ NEAA/PSG lacking serum. Cell-conditioned media was harvested after seven days, concentrated, and diafiltered against 10 mM Tris-HCl, pH 8.5. The concentrated media was loaded onto a Q-sepharose FF (Pharmacia) ion exchange column and bound material was eluted with a linear gradient of 0 to 0.5 M NaCl in 10 mM Tris-HCl, pH 8.5. Fractions were analyzed by SDS-PAGE and western blotting using a rabbit polyclonal antibody directed against residues 22–148 of the HEK4 external domain. Fractions containing HEK4-X protein were pooled, concentrated and loaded onto an S-200 (Sephaoryl S-200, Pharmacia) column. Fractions from this column were analyzed as before and those containing HEK4-X were pooled.

EXAMPLE 2

A. Purification of HEK4-X Binding Activity

We have previously described the use of the BIAcore™ instrument (Pharmacia Biosensor, Piscataway, N.J.) for the detection of receptor binding activity in concentrated cell-conditioned media (Bartley et al., supra). We used a similar strategy to screen for HEK4 receptor binding activity as described below.

The surface of a BIAcore sensor chip was activated by injection of 0.2 M 1-ethyl-3-(3-dimethylaminopropyl) carbodiimide-HCl and 0.05 M N-hydroxysuccinimide at a flow rate of 5 ul/min. Purified HEK4-X at a concentration of 250 μg/ml was applied to the activated surface in two 50 ul injections at the same flow rate. Unreacted binding sites were blocked by injection of 1M ethanolamine, pH 8.5. The surface was washed overnight in 10 mM HEPES, 150 mM NaCl, 3.4 mM EDTA, 0.005% Tween 20, pH 7.4 until the baseline was stable. Typically, immobilization resulted in 6000–8000 resonance units (RU) of HEK4-X bound to the sensor chip.

Conditioned media samples were collected from 108 cell lines grown either without fetal bovine serum (FBS) or in the presence of 0.5% FBS. Conditioned media produced under serum-free conditions was adjusted to 0.5% FBS before further processing. The media was filtered, concentrated 25-fold, and stored in aliquots at −80° C. 30 ul samples of each medium were injected onto the HEK4-X surface at a flow rate of 5 μl/min and the binding response measured 20 seconds after the conclusion of each injection. Between samples, the surface was regenerated by 10–15 μl injections of 25 mM 3-(cyclohexylamino)-1-propanesulfonic acid, pH 10.4. Concentrated conditioned media samples displaying binding of 200 resonance units or more are listed in Table 1.

TABLE 1

| Cell Line | Description | Binding (resonance units) |
| --- | --- | --- |
| HCT116 | human colon carcinoma | 911 |
| M-14 | human melanoma | 337 |
| LS174T | human colon adenocarcinoma | 316 |
| A498 | human kidney carcinoma | 274 |
| A172 | human glioblastoma | 269 |
| PK(15)1 | porcine kidney | 234 |
| JEG-1 | human choriocarcinoma | 220 |
| Y-79 | human retinoblastoma | 216 |
| HT 1080 | human fibrosarcoma | 200 |

The five conditioned media displaying the most binding were selected for further investigation. When soluble dextran was added to samples before injection to reduce non-specific binding, the signals from HCT116 and LS174T conditioned media were greatly reduced. A172 cells proved difficult to grow and were unsuitable for the large scale production of conditioned media. Based on these experiments and on pilot scale receptor affinity chromatography, the A498 cell line (ATCC No. HTB 44) was chosen as the best source of conditioned media for purification of a HEK4 binding protein.

A HEK4 receptor affinity column was prepared by immobilization of HEK4-X on CNBr-activated Sepharose 4B (Pharmacia). Purified HEK4-X was dialyzed against 0.1 M NaHCO$_3$, 0.5 M NaCl, pH 8.3 and brought to a final concentration of 2 mg/mL. Immobilization of HEK4-X was done at a ligand density of 1 mg/mL according to the method of Kenny et al. (New Protein Techniques, J. M. Walker, ed. The Humana Press, Clifton, N.J. 1988). Forty liters of A498 conditioned media produced in 0.5% serum-containing media was concentrated 40-fold, diafiltered against PBS and 0.02% NaN$_3$, and loaded onto the HEK4-CNBr sepharose column. The column was washed with PBS and bound material was eluted with 50 mM sodium acetate, 0.5 M sodium chloride, pH 4.0. Fractions were collected in 1 mM CHAPS and loaded directly on polyacrylamide gels. Gels were either stained with silver for analysis or blotted onto PVDF membranes (Problot, Applied Biosystems, Foster City, Calif.) in preparation for N-terminal amino acid sequencing (Fausset & Lu, 1991).

Figure 2B:
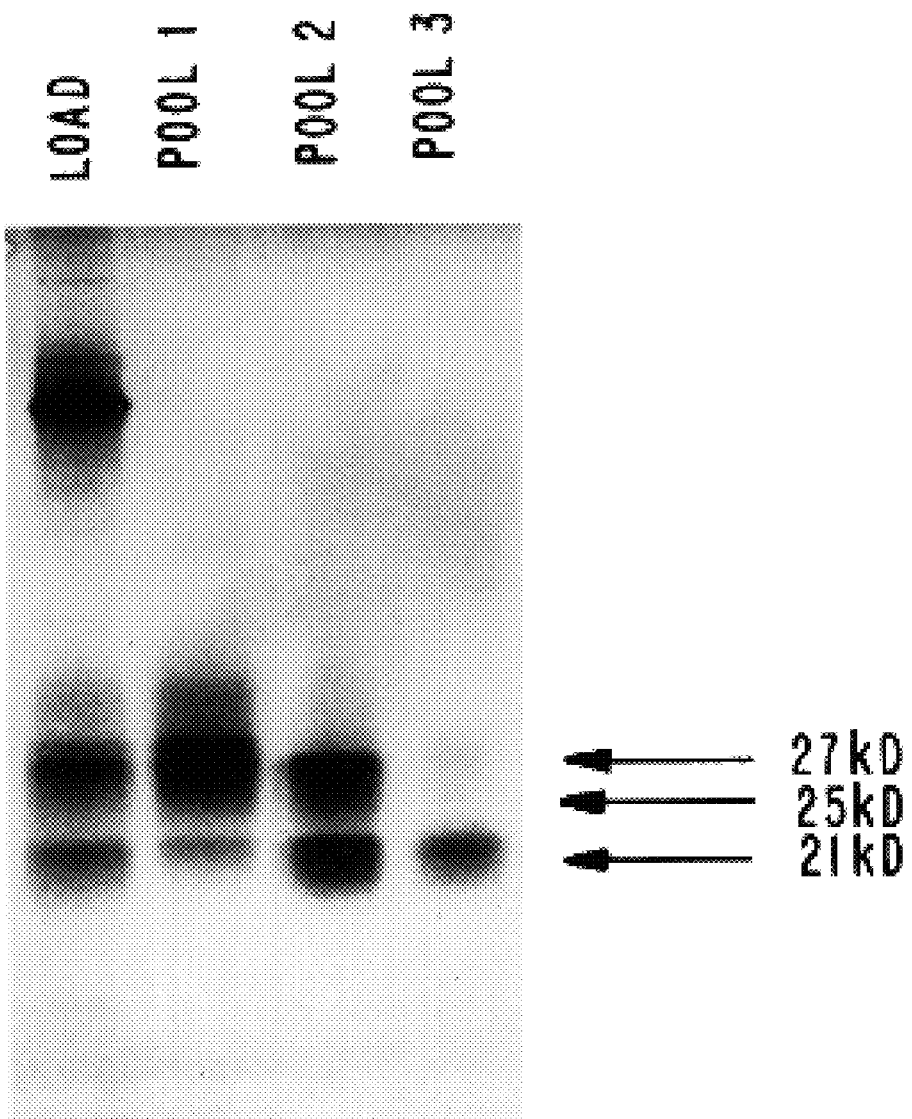

The pH 4.0 elution fractions from the HEK4-CNBr Sepharose column contained three major protein species with molecular weights of 21, 25 and 27 kD which were not apparent in the load or wash fractions. The fractions containing these 3 proteins were pooled, concentrated in the presence of CHAPS and applied to a Vydac C4 reverse phase HPLC column (4.6×150 mm). The column was eluted with a gradient of acetonitrile (26–35%) in 0.1% trifluoroacetic acid. Fractions were collected, volume reduced under vacuum, and analyzed for HEK4 binding protein. The three major peaks detected by absorbance at 214 nm were pooled and analyzed by SDS-PAGE (see FIGS. 2A, 2B). Further purification of the three isoforms of HEK4 BP was achieved by reapplying the proteins to the same C4 column.

B. Sequencing of Peptides

A sample from the initial purification of A498 cell-conditioned media was submitted for protein sequencing. The sample was analyzed on SDS-PAGE and blotted onto PVDF membrane. The gel band identified as the HEK4 binding protein was excised and analyzed for five cycles on an Applied Biosystems 477A protein sequencer. This yielded no sequence, indicating that the protein was N-terminally blocked. The sample was then treated with cyanogen bromide and reapplied to the sequencer. A tentative sequence was obtained from the cleaved sample by assuming the highest yield at each cycle to belong to the same peptide. Even given this assumption, recoveries were so small as to render the sequence unreliable after cycle 10. The sequence obtained in this manner is shown as peptide #1 in Table 2.

TABLE 2

| Peptide No. | Amino acid sequence |
| --- | --- |
| 1 | Val-Asn-Phe-Asp-Gly-Tyr-Ser-Ala-Arg-Asp (SEQ ID NO: 5) |
| 2 | Val-Phe-Asp-Val-Asn-Phe-Lys-Val-Glu-X-Ser-Leu-Glu-Pro-Ala-Asp (SEQ ID NO: 6) |
| 3 | Ala-Val-Ala-Asp-Arg-Tyr-Ala-Val-Tyr-Trp-Asn-Ser-Ser-Asn-Pro-Arg-Phe-Gln-Arg-Gly-Asp-Tyr-His-Ile-Ile-Val-X-Ile-Asn-X-Tyr (SEQ ID NO: 7) |

Subsequent analysis of samples cleaved by cyanogen bromide, then separated by SDS-PAGE indicated that position 9 of peptide #1 was a cysteine residue and position 6 of peptide #2 was aspartic acid. Position 25 of peptide #3 was subsequently found by DNA sequencing to be aspartic acid. The sequence data shown in peptides #2 and #3 in Table 2 was obtained by analysis of tryptic digests of the protein followed by separation of the resulting peptides on a microbore C4 column. These experiments were done with larger amounts of starting material and therefore yielded more reliable sequence and allowed 20–30 cycle sequencing runs. Comparison of the peptide sequences in Table 2 with B61 suggests that they represent fragments of a related protein. We therefore conclude that the HEK4 binding protein is another ligand for the human EPH-like kinase sub-family.

EXAMPLE 3

A. Cloning and Sequencing of cDNA Encoding HEK4 Binding Protein

The amino acid sequences obtained from HEK4 BP peptides as shown in Table 2 were used to design oligonucleotide primers. Primers 702-3 and 633-11 were used in a PCR reaction with random primed A498 cDNA as a template.

702-3) 5' GAYMGNTAYGCNGTNTAYTGG 3' (SEQ ID NO:8)

633-11) 5' RTANCCRTCRAARTTNACCAT 3' (SEQ ID NO:9) The 175 base pair fragment amplified by these primers was sequenced and found to be closely related to B61. This fragment was then radiolabeled with $^{32}P$ by random priming and used as a probe to screen a cDNA library for clones containing the full length HEK4 BP cDNA. An oligo-dT primed human placental cDNA library purchased from Stratagene (La Jolla, Calif.) was plated at a density of 30,000 plaques/150 mm plate. Replicas of the plaques arrayed on the plates were made on GeneScreen™ hybridization transfer membranes (New England Nuclear, Boston, Mass.) as directed by the manufacturer. Two replica filters were made for each plate. Filters were pre-hybridized in 6× SSC, 1× Denhardts buffer, 50 ug/ml salmon testis DNA, 1% SDS at 65° C. for 4 hours followed by hybridization with the $^{32}P$-labeled probe for 12 hours under the same conditions. Following hybridization, filters were washed two times, 1 hour each, in 0.2× SSC, 0.5% SDS at 65° C. and exposed to Kodak XAR film overnight with an intensifying screen. Comparison of the two filters made from each plate showed that five plaques were positive on both replicas. The phage around each positive plaque were removed, resuspended in buffer, and replated at a lower density to produce well-separated plaques for secondary screening. Individual plaques which were positive upon rescreening (using the same method as the primary screen) were picked. The inserts from these phage were transferred into the pBluescript plasmid by in vivo excision as described by the manufacturer (Stratagene). Three of the five inserts were identical and contained the entire coding region of HEK4 BP while the other two represented overlapping clones. A consensus sequence was assembled using data from the three inserts containing the entire coding region and is shown in FIGS. 3A–C.

The HEK4 BP cDNA sequence predicts a protein of between 213 and 228 amino acids, depending on which of three possible initiator codons is utilized. Based upon rules for translation of vertebrate mRNAs (Kozak Cell 44, 283–292 (1986)), the third in-frame ATG is an unlikely initiator, while the first ATG, being the farthest upstream is the most likely to be the principal initiation codon. As for B61, HEK4 BP has hydrophobic amino acids on both the amino and carboxy termini. These probably function as a secretion signal sequence and a membrane anchor, respectively. Like B61, HEK4 BP apparently has both soluble and membrane bound forms. Although we were not able to obtain N-terminal protein sequence data, we would predict cleavage of the signal peptide to yield a mature protein with serine at position 1 (FIGS. 3A, 3B, 3C). Based on peptide mapping and mass spectrometric analysis, proline-179 (FIGS. 3A–C) appears to be the C-terminal amino acid in the major soluble form found in A498 cell-conditioned media. An alternate form with alanine-177 (FIGS. 3A–C) at the C-terminus was also detected.

B. Expression of Recombinant HEK4 BP

The HEK4 BP cDNA clone shown in FIGS. 3 was inserted into the plasmid vector pDSRα for expression mammalian cells. The recombinant plasmid was transfected into Chinese hamster ovary (CHO) cells by calcium phosphate precipitation and cells containing the plasmid were selected by growth in DMEM (high glucose, GIBCO, Bethesda, MD), 1× penicillin/streptomycin/glutamine (PSG), 1× non-essential amino acids (NEAA) containing 10% fetal bovine serum (FBS), but lacking HT supplement (HT supplement: 10 mM sodium hypoxanthine, 1.6 mM thymidine). The expression of HEK4 BP in several clones was assessed by the level of HEK4-receptor binding activity in each clone's cell-conditioned media as determined by BIAcore (Pharmacia Biosensor, Piscataway, N.J.). This correlated well with the level of HEK4 BP mRNA in the clones as determined by Northern blot hybridization. One clone, CHO/HL6, was a significantly better producer of recombinant HEK4 BP than the others and was chosen for further work. Expression of HEK4 BP by CHO/HL6 was enhanced 2 to 4-fold by treatment with increasing amounts of methotrexate up to 100 nM over a period of several weeks. Following amplification, cells expressing HEK4 BP were expanded and transferred to roller bottles for production of conditioned media to be used as a source for purification of the recombinant protein. A total of 100 roller bottles were seeded with CHO/HL6 cells at $10^7$ cells per bottle. Cells were grown until confluent (approximately 4 days) in DMEM (high glucose, GIBCO, Bethesda, Md.), 1× PSG, 1× NEAA, and 10% FBS. Following the growth phase, the media was removed replaced with the same media but with 0.5% rather than 10% FBS. After 3 days, the media was collected, filtered to remove any cell debris, and stored frozen at –80° C.

EXAMPLE 4

Purification of Recombinant HEK4 BP

Figure 4A:
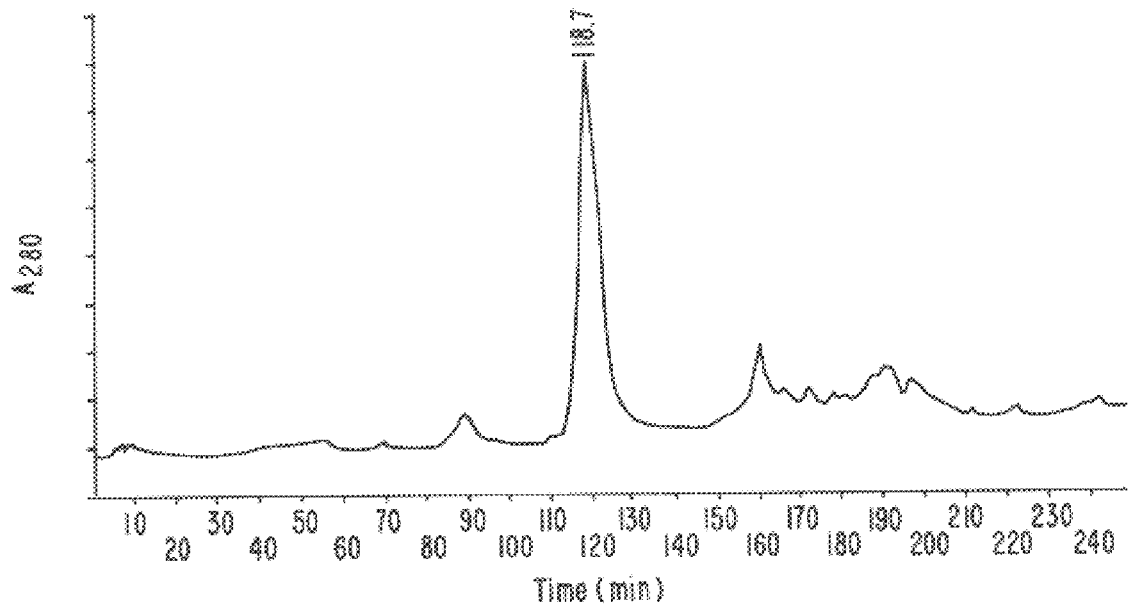
FIGS. 4A and 4B. Purification of recombinant HEK-4 binding protein. C4 Reverse Phase HPLC column profile of recombinant HEK4 BP (A); SDS-PAGE analysis of C4 fractions in the vicinity of the $A_{214}$ peak (B). Fractions are identified by elution times from the C4 column.
Figure 4B:
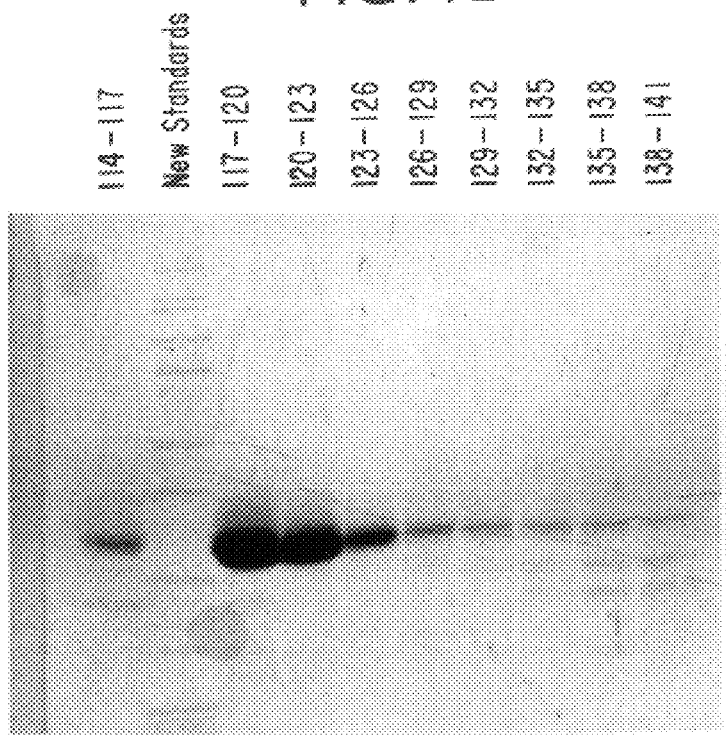

Approximately 20–25 liters of conditioned medium from CHO/HL6 cells were thawed at room temperature and filtered. The medium was concentrated and diafiltered against 10 mM Tris-HCl, pH 8.5 (4° C.) using a 10,000 molecular weight cut off membrane. The diafiltrate was applied to a column of Q-Sepharose, High Performance and subsequently eluted with a linear gradient of NaCl (0–0.3 M) in 10 mM Tris-HCl, pH 8.5. Fractions were analyzed for the presence of HEK4 BP by immunoblotting using an antibody generated against unfolded HEK4 BP produced in *E. coli*, or by binding to HEK4 receptor immobilized on a BIAcore sensor chip. Fractions containing HEK4 BP were pooled, concentrated and applied to a gel filtration column. (Superdex 75, 5×85 cm, PBS, 3 mL/min). Fractions containing HEK4 BP were further purified by C4 reverse phase HPLC (Vydac 214TP 4.6×250 mm, 2.9 mL/min) using an acetonitrile gradient (22–44%) in 0.1% trifluoroacetic acid. The column profile and SDS-PAGE analysis of peak fractions are shown in FIGS. 4A, 4B. Fractions were evaporated under vacuum and formulated in 0.25 M Tris-HCl, 2 mM CHAPS, pH 7.5.

EXAMPLE 5

A. Production of Antibodies to HEK4 Receptor

Antibodies directed against the HEK4 receptor extracellular domain were produced using standard methods (Harlow and Lane, *Antibodies: A Laboratory Manual* Cold Spring Harbor Laboratory Press, Cold Spring Harbor, N.Y. (1988)). cDNA encoding amino acids 22–148 of the HEK4 receptor was inserted into the pATH vector (Yansura, 1990) in the same translational reading frame as the TrpE gene. The resulting plasmid was introduced into an *E. coli* host strain resulting in expression of the HEK4/TrpE fusion protein. Bacterial cell lysates were fractionated by preparative SDS-PAGE and the band containing the HEK4/TrpE fusion was excised. The crushed gel slice was used to immunize rabbits according to standard protocols (Harlow and Lane, supra). The antisera generated by this method recognized both the HEK4/TrpE antigen and recombinant HEK4-X produced in CHO cells.

Antibodies to the C-terminal 12 amino acids of the HEK4 receptor (sequence is cys-leu-glu-thr-gln-ser-lys-asn-gly-pro-val-pro-val) were produced by the same method (Harlow and Lane, supra) using a synthetic peptide chemically linked to keyhole limpet hemocyanin (KLH) as the antigen. The antiserum was purified by passage over a column upon which peptide antigen had been immobilized using a SulfoLink kit (Pierce, Rockford, Ill.). These antibodies were able to specifically recognize HEK4 receptor by Western blots.

B. Production of Antibodies to HEK4 BP

HEK4 BP cDNA as shown in FIG. 3 was used as a template for PCR with primers 819-31 and 819-28 to produce a polypeptide fragment coding for amino acids 1–179 of HEK4 BP (FIGS. 3A, 3B, 3C).
819-31) 5' GGAGGACATATGAGCCAGGAC-CCGGGCTCCAAG 3' (SEQ ID NO:10)
819-28) 5' GAAGAAGGATCCCTATGGCTCGGCT-GACTCATGTAC 3'
(SEQ ID NO:11)

The PCR fragment was cloned into the expression vector pCFM1656 using the NdeI and BamHI sites included in the primers. The resulting recombinant plasmid was transformed into *E. coli* FM5 (ATCC No. 53911) and the truncated HEK4 BP was expressed as insoluble inclusion bodies. The inclusion bodies were solubilized and the HEK4 BP fragment purified by SDS-polyacrylamide gel electrophoresis was used as an antigen in rabbits. The antisera was generated and characterized as described (Harlow and Lane, supra) and recognized HEK4 BP expressed in CHO cells by Western blot analysis.

EXAMPLE 6

A. Expression Pattern of the HEK4 Receptor

The expression of HEK4 receptor mRNA in rat and human tissues has been previously reported in co-pending and commonly owned U.S. Ser. No. 08/229,509, relevant portions of which have been incorporated herein by reference. The results of these studies are summarized in Table 3.

TABLE 3

Tissue Distribution of HEK4 Receptor

| Tissue: | Human | Rat |
|---|---|---|
| Brain | ++ | + |
| Heart | + | bd |
| Kidney | + | bd |
| Liver | + | bd |
| Lung | + | + |
| Muscle | + | bd |
| Ovary | nt | bd |
| Pancreas | + | nt |
| Placenta | +++ | nt |
| Stomach | nt | bd |
| Testis | nt | + |
| Thymus | nt | bd | bd = below detection
nt = not tested

In the human tissues studied, HEK4 receptor mRNA is most abundantly expressed in placenta, with lower levels in heart, brain, lung, and liver. Previous studies on HEK4 receptor mRNA in cell lines found expression in one pre-B cell line and two T-cell lines (Wicks et al. 1992).

B. Expression Pattern of HEK4 BP

Figure 5:
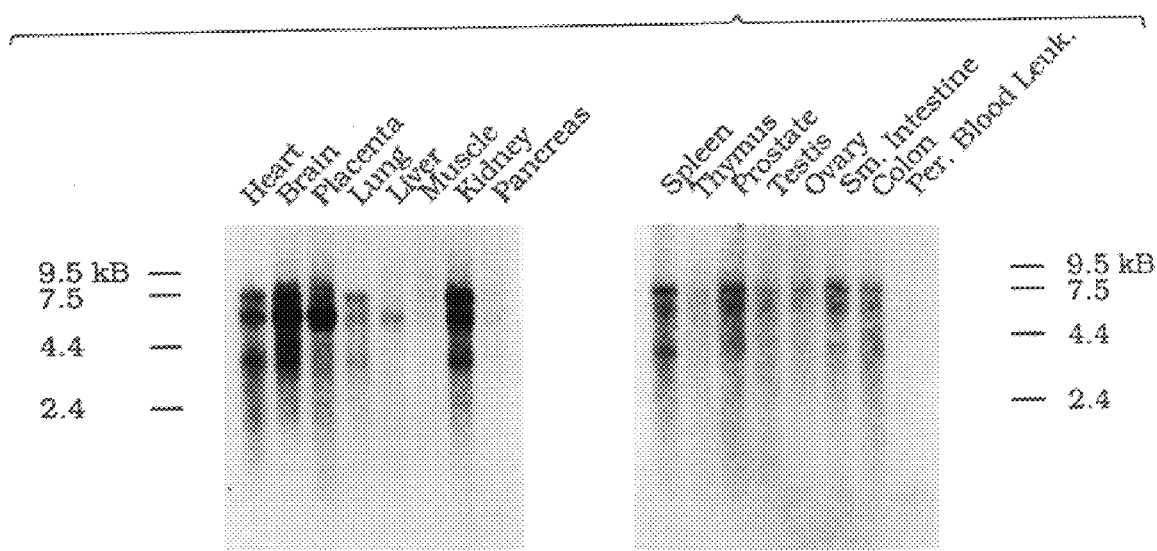
FIG. 5. Expression of HEK-4 binding protein in human tissues. The expression of HEK-4 binding protein mRNA in human tissues was examined by Northern blot analysis as described in Example 6. A blot containing 2 μg of polyA+ mRNA isolated from each of several tissues was purchased from Clontech (Palo Alto, Calif.) and hybridized with a $^{32}$P-labeled HEK-4 binding protein cDNA probe.

The expression of HEK4 BP mRNA in human tissues was examined by Northern blot analysis. A Northern blot containing 2 μg of polyA$^+$ from each of the tissues indicated was purchased from Clontech (Palo Alto, Calif.) and hybridized with a $^{32}$P-labeled HEK4 BP probe. As shown in FIG. 5, HEK4 BP mRNA is expressed at high levels in human adult brain, kidney, and placenta. Readily detectable levels can also be found in heart, lung, liver, spleen, prostate, testis, ovary, small intestine, and colon. The presence of HEK4 BP mRNA in many different tissues is consistent with the idea that this factor is important for the differentiation, development, and/or maintenance of a variety of cell types.

EXAMPLE 7

A. HEK4 BP Activation of EPH Subfamily Receptors by Cell-Cell Autophosphorylation The hallmark of receptor activation for all known receptor protein-tyrosine kinases is autophosphorylation (van der Geer et al., supra). To determine whether HEK4 BP can activate HEK4 receptor, a cell-cell autophosphorylation assay was performed. Recipient cells were CHO cells transfected with HEK4 receptor cDNA which had been serum-starved by incubation in media with 0.5% serum for 16 hours. The donor cells were CHO cells transfected with HEK4 BP cDNA (see Example 3B) or CHO cells that had been transfected with vector alone. Donor cells were scraped from the surface of their growth vessel in phosphate-buffered saline and added to recipient cells for 30 minutes at 37° C. After washing, the recipient cells were lysed in modified RIPA buffer (10 mM sodium phosphate, pH 7.4, 150 mM sodium chloride, 0.1% sodium dodecyl sulfate, 1% NP-40, 1% deoxycholate, 10 mg/ml aprotinin, 5 mM EDTA, 200 mM sodium orthovanadate). Receptors were immunoprecipitated from the cell lysate and prepared for SDS polyacrylamide gel electrophoresis as previously described (Bartley et al., supra). After electrophoresis and electroblotting to membranes, the immunoprecipitates were probed with antiphosphotyrosine antibodies (4G10, UBI, Lake Placid, N.Y.). Immune complexes were detected by horse-radish peroxidase conjugated secondary reagents using chemiluminescence as described by the manufacturer (ECL, Amersham). As shown in FIGS. 6A, 6B cells expressing HEK4 binding protein were able to stimulate tyrosine phosphorylation on both the HEK and ECK receptors. Control cells did not stimulate the phosphorylation of either receptor. The results demonstrate that HEK4 BP can activate both the HEK4 and the ECK receptors.

B. Activation of HEK4 Receptor by Soluble HEK4 BP

To determine whether soluble recombinant HEK4 BP could activate the HEK4 receptor, CHO cells transfected with HEK4 receptor cDNA were treated with conditioned media from CHO cells expressing HEK4 BP (see Example 3B) or with purified recombinant HEK4 BP (see Example 4). The cells were serum-starved by incubation in media with 0.5% serum for 16 hours prior to the treatments. Treatments were for 30 minutes at 37° C., after which the cells were lysed in modified NP40 buffer (50 mM Tris, pH 8.0, 150 mM sodium chloride, 1% NP40, 10 mg/ml aprotinin, 5 mM EDTA, 200 mM sodium orthovanadate), HEK4 receptor was immunoprecipitated, and prepared for SDS polyacrylamide gel electrophoresis as previously described (Bartley et al., supra). After electrophoresis and electroblotting to membranes, the immunoprecipitates were probed with antiphosphotyrosine antibodies (4G10, UBI, Lake Placid, N.Y.). Immune complexes were detected by horseradish peroxidase conjugated secondary reagents using chemiluminescence as described by the manufacturer (ECL, Amersham). As shown in FIGS. 7A, 7B soluble recombinant HEK4 BP in conditioned media and after purification activated HEK4 receptor. This activation was enhanced by pretreatment of conditioned media or purified HEK4 BP with the antibodies of Example 5B which had been affinity purified on a HEK4 BP column. Antibodies (~50 μg/ml) were incubated with conditioned medium or purified HEK4 BP at 4° for 1 hr. prior to treatment of CHO cells expressing HEK4 receptor.

EXAMPLE 8

Affinity of HEK4 BP for EPH-like Receptors

A competition assay was used to measure differences in HEK4 BP binding to different EPH-like receptors. Purified HEK4 BP was incubated with various concentrations of either HEK4, HEK8 or ECK soluble receptors and binding of the mixture to immobilized HEK4 receptor was analyzed by BIAcore. The concentration of soluble receptor that inhibited HEK4 BP binding by 50% is termed IC50. IC50 values allow a comparison of the relative affinity of HEK4 BP for related receptors.

Figure 8:
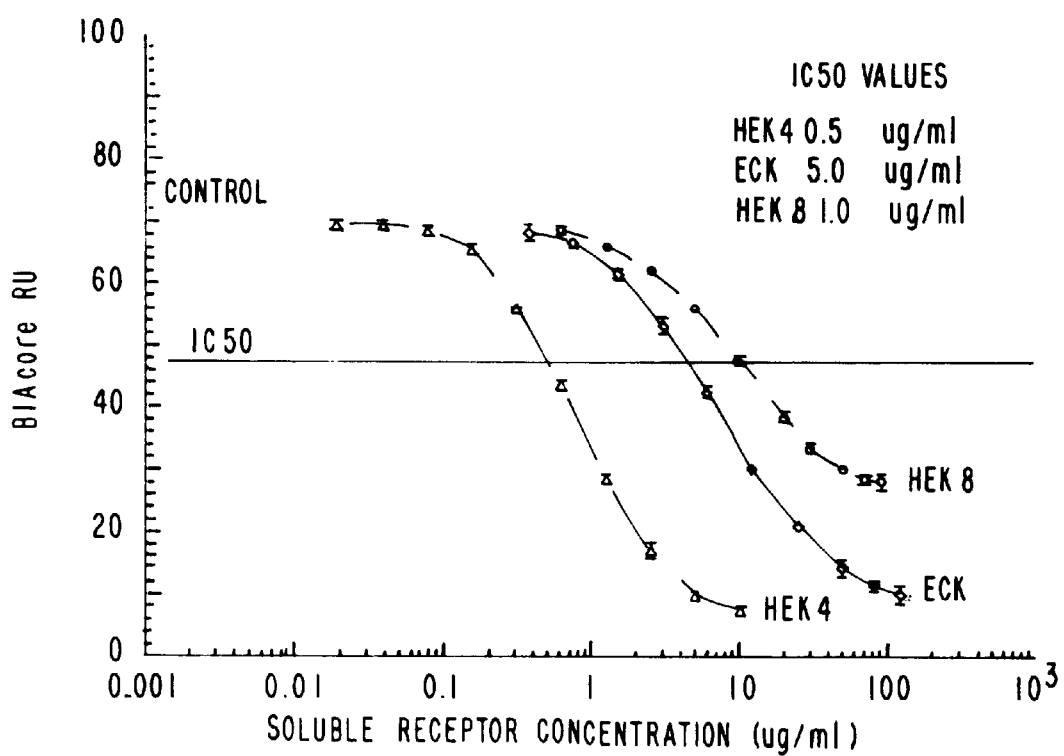
FIG. 8. Relative affinity of HEK4 BP for HEK 4, ECK and HEK8 receptors. A competition assay for measuring binding of HEK4 BP to immobilized HEK4 receptor in the presence of increasing concentrations of soluble HEK4, ECK and HEK8 receptors was performed as described in Example 8. The line identified as "IC 50" is drawn at an RU value corresponding to a HEK4 BP concentration which is 50% of the control (no competitor) RU value.

IC50 values were determined as follows. Analysis of HEK4 BP binding to immobilized HEK4 receptor showed a linear response in the range 60 to 500 ng/ml. Various amounts of the purified extracellular domains of HEK4, ECK, or HEK8 were incubated with 0.250 μg/ml HEK4 BP prepared as described in Example 4 in solutions containing 100 μg/ml BSA, 10 mM HEPES, 0.15M NaCl, 3.4 mM EDTA, and 1 mg/ml soluble dextran, pH 7.4. These solutions were incubated for at least 30 minutes at 3° C. prior to injection. Protein concentrations of receptor stocks were confirmed by BCA protein assay. Duplicates of each sample were run in parallel with standard curves on two different days. All surfaces were regenerated to within 10 RU of baseline with 25 mM CAPS and 1 M NaCl pH 10.4. The mean binding response was plotted versus soluble receptor concentration (FIGS. 8) providing IC50 values of 0.55 ug/ml for HEK4, 5.0 μg/ml for ECK, and 10.5 μg/ml for HEK8. Thus, HEK4 BP preferentially binds HEK4 receptor compared to two other EPH family members, ECK and HEK8.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. An isolated nucleic acid encoding a polypeptide which binds to at least a HEK4 receptor wherein the nucleic acid is selected from the group consisting of:
   a) the nucleic acid having the sequence shown in SEQ ID NO:1 and its complementary strand;
   b) nucleic acids which hybridize under conditions of 6×SSC and 65° C. and remain hybridized under conditions of 0.2×SSC and 65° C. with the coding region of SEQ ID NO: 1; and
   c) nucleic acids which are degenerate to nucleic acids set forth in (a) and (b).

2. The nucleic acid of claim 1 which is cDNA, genomic DNA or synthetic DNA.

3. The nucleic acid of claim 1 which comprises one or more codons preferred for expression in *Escherichia coli*.

4. An expression vector comprising the nucleic acid of claim 1.

5. A procaryotic or eucaryotic host cell stably transformed or transfected with the vector of claim 4.

6. The host cell of claim 5 which is a CHO cell.

7. The host cell of claim 5 which is *Escherichia coli*.

8. A process for the production of a polypeptide which binds at least a HEK4 receptor comprising growing under suitable nutrient conditions a procaryotic or eukaryotic host cell transformed or transfected with the nucleic acid of claim 1 and isolating the polypeptide product of the expression of the nucleic acid.

* * * * *